US011978353B2

(12) United States Patent
Vogel et al.

(10) Patent No.: US 11,978,353 B2
(45) Date of Patent: May 7, 2024

(54) DEVICE, SYSTEM AND METHOD FOR ENTRAINMENT AND TRAINING OF THE HUMAN BRAIN

(71) Applicants: Wolfgang Vogel, Herdwangen-Schönach (DE); Amira Jaber, Pully/Vd (CH)

(72) Inventors: Wolfgang Vogel, Herdwangen-Schönach (DE); Amira Jaber, Pully/Vd (CH)

(*) Notice: Subject to any disclaimer, the term of this patent is extended or adjusted under 35 U.S.C. 154(b) by 739 days.

(21) Appl. No.: 17/260,061

(22) PCT Filed: Jul. 11, 2019

(86) PCT No.: PCT/EP2019/068768
§ 371 (c)(1),
(2) Date: Jan. 13, 2021

(87) PCT Pub. No.: WO2020/011958
PCT Pub. Date: Jan. 16, 2020

(65) Prior Publication Data
US 2021/0280080 A1   Sep. 9, 2021

(30) Foreign Application Priority Data
Jul. 13, 2018   (EP) .................................. 18183530

(51) Int. Cl.
*G09B 19/00*   (2006.01)
*G09B 9/00*   (2006.01)
*G16H 20/70*   (2018.01)

(52) U.S. Cl.
CPC ............... *G09B 19/00* (2013.01); *G09B 9/00* (2013.01); *G16H 20/70* (2018.01)

(58) Field of Classification Search
CPC .............................. G09B 19/00; A61M 21/00
See application file for complete search history.

(56) References Cited

U.S. PATENT DOCUMENTS 6,042,548 A    3/2000  Giuffre
6,475,162 B1   11/2002 Hu
(Continued)

FOREIGN PATENT DOCUMENTS

AU    2006252068 A1    1/2007
CN      106137135 A    11/2016
(Continued)

OTHER PUBLICATIONS

Journal of Biomedical Engineering, Issue 3, Publication date: Jun. 30, 2004, pp. 410-415.
(Continued)

*Primary Examiner* — Kurt Fernstrom
(74) *Attorney, Agent, or Firm* — MARSHALL, GERSTEIN & BORUN LLP

(57) ABSTRACT

A biocybernetics based system for detecting the biofeedback of human central nervous system activity and its optimization includes a non-invasive human brain interface device for the stimulation of the human brain using weak pulsed electromagnetic fields, a multi-sensor detection unit for the real-time measurement of various states of the central and autonomic nervous system, linked to a processing and feedback software supported by a database. Optimization processes are based on bio-cybernetic regulation, controlled by intrinsic feedback loops, generating measurable output for optimizing brain stimulation parameters as well as sensing feedback output to the human subject, in the form of visual, auditory, tactile, and highly immersive content related output including simulations in virtual and augmented reality.

15 Claims, 10 Drawing Sheets

(56) References Cited

U.S. PATENT DOCUMENTS

| | | | |
|---|---|---|---|
| 9,427,598 B2* | 8/2016 | Pilla | A61N 1/40 |
| 10,417,926 B2* | 9/2019 | Bachani | A61B 5/0205 |
| 11,020,603 B2* | 6/2021 | Ansari | G06K 19/027 |
| 11,322,042 B2* | 5/2022 | Siever | G09B 21/00 |
| 11,369,770 B2* | 6/2022 | Shin | A61N 1/36034 |
| 11,723,579 B2* | 8/2023 | Poltorak | A61B 5/369 |
| | | | 607/72 |
| 2002/0188164 A1* | 12/2002 | Loos | A61N 2/00 |
| | | | 600/9 |
| 2003/0073899 A1 | 4/2003 | Ruohonen et al. | |
| 2007/0191727 A1 | 8/2007 | Fadem | |
| 2012/0101327 A1* | 4/2012 | Dissing | A61P 25/16 |
| | | | 564/336 |
| 2013/0338738 A1* | 12/2013 | Garcia Molina | G09B 19/00 |
| | | | 607/90 |
| 2019/0054308 A1* | 2/2019 | Verma | A61N 2/006 |
| 2019/0336782 A1* | 11/2019 | Shealy | A61N 2/02 |
| 2020/0009423 A1 | 1/2020 | Della Carit | |
| 2020/0410890 A1* | 12/2020 | Yamada | A61B 5/055 |

FOREIGN PATENT DOCUMENTS

| | | |
|---|---|---|
| CN | 107346179 A | 11/2017 |
| CN | 107497051 A | 12/2017 |
| EP | 3064130 A1 | 9/2016 |
| JP | 2009022660 A | 2/2009 |

OTHER PUBLICATIONS

Office Action issued in Chinese Application No. 201980057155.X dated Jul. 27, 2022.

International Search Report issued in PCT Patent Application No. PCT/EP2019/068768 dated Aug. 6, 2019.

Written Opinion issued in PCT Patent Application No. PCT/EP2019/068768 dated Aug. 6, 2019.

Li Rihui et al: "Blood oxygenation changes resulting from sub-threshold high frequency repetitive transcranial magnetic stimulation", 2017 39th Annual International Conference of the IEEE Engineering in Medicine and Biology Society (EMBC), IEEE (2017).

Balconi, M. "Brain plasticity and rehabilitation by using Near-Infrared Spectroscopy", *Neuropsychological Trends*, No. 19 (2016).

Wang, K. et al: "Real-time fNIRS signal acquisition system: Compatible with TMS" 2017 Chinese Automation Congress (CAC), IEEE (2017).

* cited by examiner

DEVICE, SYSTEM AND METHOD FOR ENTRAINMENT AND TRAINING OF THE HUMAN BRAIN

BACKGROUND

Brain Fitness is a major component of optimum human performance and general health. Brain fitness means having a positive sense of how we feel, think, and act. It means better mental performance and clarity, emotional balance, and a sense of well-being allowing us to enjoy life. The impact of the demographic change, growing demands at the workplace and increasing challenges of a multi-media dominated life are severe social, economic and health threats. Statistical data on the increasing number of people living with dementia and the related costs are confirmed by the latest World Alzheimer Report. Similar data regarding the rising number of stress-related diseases with its burden on the global economy and socio-individual consequences are reported by the WHO.

As far as physical fitness training is concerned, mature concepts are established providing measurable and documented results. A systematic and regular training prevents cardio vascular diseases as well as different impairments related to overweight or physical inactivity. However, training concepts based on the improvement of physical fitness do not sufficiently address the optimization of cognitive functioning, stress resilience and other factors such as mental clarity mainly influenced by an optimized performance of the brain.

During the last decade, scientists have proven that the brain is able to alter neuronal pathways when exposed to physical stimuli, called the neuroplasticity of the brain! Methods leading to a measurable and sustainable improvement of brain functioning based on the latest scientific findings are currently at a clinical research state and not accessible for the general population.

Brain training systems that are commercially available are either based on a pure software-based solution or on a commodity instrument working with brainwave sensors based on EEG, with limited application range or alternatively an instrument that stimulates the brain with electricity, or pulses of sound and light, so called mind machines.

These systems are not satisfying the needs of a targeted, systematic and effective brain fitness training in a commercial service environment, comparable with today standards of physical fitness and personal training. A method for training and optimizing cognitive performance as well as stress resilience in a professional setting must be effective, measurable, personalized and affordable to a wider population. Improvements should be sustainable based upon a regular training.

Looking for methods and systems that fulfil the aforementioned performance criteria for a commercial offering in the area of Brain Fitness Training, technology and methods stemming from the medical and therapeutic sector have to be considered.

Measuring, monitoring and interpreting activities of the central and autonomous nervous system of a human subject has become of interest far beyond the medical field up to now.

What biofeedback-based methods for stress reduction are concerned, sensors monitoring changes in the activation level of the autonomous nervous system play a key role. Recording and interpreting of signals from the autonomous nervous system are rather simple from a technology point of view. The measurement of the Heart Rate Variability (HRV) or the Galvanic Skin Response (GSR) are common methods to detect small changes in the sympathetic/parasympathetic loop.

However, measuring signals and interpreting brain patterns has always been a much bigger challenge from both a technological and operational perspective.

The method of choice to monitor activities of the brain has been electroencephalography (EEG) for many decades. High temporal resolution and the possibility to detect oscillations of neural activities offers a high degree of information. Since a couple of years modern computing technology enables the real time monitoring of the time and frequency domain at different brain locations via mathematical operations such as the Fast Fourier Transformation. Multi-channel quantitative electro encephalography (QEEG) devices are state-of-the-art in neurological diagnosis today.

Software programs enhance the functionality from pure device control, data processing and result evaluation to real time feedback applications providing the human subject with constant information about his brain state and performance via intrinsic feedback loops. Those type of applications are generally termed as "neurofeedback". Neurofeedback has emerged from clinical research to applied psychology treating several mental disorders and malfunctions.

Taking advantage of a system outside regulated environments, i.e. for example methods of brain fitness training such as enhancement of cognitive performance or the prevention of age-related cognitive decline as described in the present invention below, there are several obstacles to overcome:

EEG as a real time brain monitoring device creates movement artefacts especially if the EEG electrodes are located on the forehead. While these positions are crucial for the training of cognitive function, it is a big challenge to overcome for training human subjects, especially in a fitness related environment. The use of near infrared spectroscopy (NIRS) as an alternative optical brain monitoring device overcomes those limitations. NIRS has proven to be more robust towards movement artefacts then EEG. The history of using NIRS as a method for neurofeedback goes back to the 1994 when a method called hemoencephalography biofeedback was described in U.S. Pat. No. 5,995,857. The hemoencephalography device utilizes a simple one-sensor-one-detector headband and measures changes of metabolic brain activities related to the increase or decrease of cerebral blood-flow.

Operator skill requirement of current systems for clinical and therapeutic use are a serious drawback for the implementation in a non-regulated environment. Methods require configuration of multiple parameters due to the absence of fully automated routines, the correct positioning of commonly used EEG sensors on the human subject to ensure that the minimum impedance level is met, is yet another operator challenge to overcome.

Convenience Factors: Potential users of a brain training fitness method in a recreational or performance-oriented facility demand an efficient and convenient process and won't accept the common time consuming and unpleasant procedure of fixing EEG electrodes on the scalp by means of a conductive gel, whereas in a medical consultation they will. Devices equipped with dry multi-channel EEG sensors that meet the required performance specifications are by far too expensive for a commercial implementation outside medical centres.

Success Rate and Sustainability: Neurofeedback controlled brain optimization works with closed feedback loops presenting the human subject with ongoing reward/non-reward signals. In that way the brain learns its optimum function to master a defined cognitive task. Neuroplasticity comes into play that induces permanent changes in neurological pathways which leads to a long-lasting change after several training sessions. A recent open access publication (van Doren et al., European Child Adolescent Psychiatry https://doi.org/110.1007/s00787-018-1121-4 published online 14 Feb. 2018) analyzed sustained effects of neurofeedback in ADHD. Within this review and meta-analysis 10 relevant Neurofeedback related studies are compared with control studies. The improvements of the Neurofeedback groups assessed at a follow-up period of 2-12 months are comparable to the groups that received active treatment (e.g. medication).

However, it requires that the brain overcomes a certain threshold to get into the required stage. Human subjects that suffer from stress related symptoms or mild cognitive impairment are usually not in the right state to concentrate on a feedback method, thus limiting the chances of success.

An alternative to the so far discussed concept of neurofeedback-based brain training and optimization, are non-invasive brain stimulation methods. Most common in a medical environment are tDCS (transcranial direct current stimulation) and rTMS (repetitive transcranial magnetic stimulation). The latter is an FDA approved method for the alternative treatment of certain psychiatric disorders. Both methods are based on the principal to alter neural activation by either engaging or disengaging certain areas of the brain. Both methods are not suitable for applications in a personal brain training environment outside the medical practise for the reasons of safety, costs and the lack of applicability for a trained operator without a medical qualification.

Brain entrainment is another mechanism of stimulating the brain. Brain entrainment is induced by oscillatory signals in the form of pulsed light, sound or electromagnetic fields at a predefined frequency. It has been proven that the brain will mimic the frequency pattern applied by getting into resonance. The effect has been described as Frequency Following Response (FFR) by Chaieb et al., Frontiers in Psychiatry vol. 6, art. 70 doi:10.3389/fpsyt.2015.00070 published 12 May 2015) and is inter alia the subject of U.S. Pat. No. 5,356,368.

Non-invasive brain stimulation as well as brain entrainment have temporal effects on the alteration of brain patterns that usually last for a couple of hours. However, improvements that last for a longer period time have not been sufficiently proven yet. A scientific review and meta-analysis about the effects of non-invasive brain stimulation on cognitive functioning in healthy aging stated that most studies examined the effects only after the end of the stimulation period, while follow-up cognitive assessments 1 to 6 months post stimulation is limited with varying results (Hsu et al. Neurobiol. Aging 2015 August; 36(8): 2348-2359 doi: 10.1016/j.neurobiolagin.2015.04.016).

SUMMARY OF THE DISCLOSURE

Since systems and methods in the prior art are either not suitable to apply outside a regulated environment for multiple reasons, as discussed above; or do not meet the performance requirements for an effective brain fitness training, there is a need for providing a novel human brain interface method, a device and a system which overcomes those limitations and disadvantages in the prior art.

Specifically, the following objectives should be met (1) A combination of controlled feedback training and brain conditioning to provide sustainable training effects for a range of human subjects who differ in their mental and emotional state.

(2) Flexible and adaptable training methods to meet the requirements of cognitive skill training for elderly people as well brain performance training in specific sports and business situations, helping people to improve in their specific daily challenges (3) A system and device that is easy to set-up, robust, convenient for the users and affordable for a non-clinical environment, but is as efficient, safe and flexible at the same time.

(4) A system specifically designed for a use in motion and mobile with wireless communication and sensors that are robust towards movements.

This problem is solved in a first aspect by a human brain interface device with a housing, comprising a plurality of compound units, wherein each compound unit comprises:
 a first measurement unit, for the detection of real time optical signals, wherein the measurement unit has means for near-infrared spectroscopy; and
 an entrainment unit for the generation of weak pulsed electromagnetic fields.

The present invention makes use of the "neurofeedback" model and is based on the model of "operant conditioning" and brain self-regulation, taking advantage of the neuroplasticity of the brain.

The device according to the invention comprises a plurality of compound units. Each of those units integrate several functions, i.e. at least the function of non-invasive brain stimulation or brain entrainment and the real time measurement of brain activities. Further functions may also be comprised within specific embodiments as described below. Therefore, the compound unit may also be termed as "multiple compound unit" which is used in the description synonymously.

In a preferred embodiment, the entrainment unit is a solenoid, preferably a cylindrical solenoid, emitting weak pulses of electromagnetic fields, whereas the measurement component is based on optical detection of alterations in cerebral blood flow via hemoencephalography. In one specific embodiment, the cylindrical solenoids have an outer diameter of 2.5 cm (height 2 cm) with an open cavity of d=4 mm. The inner cavity 505 serves as a light guide where the optical fiber is placed.

In one specific embodiment, the first measurement unit is a spring loaded 507 detector optode 506 in order to ensure skin contact.

One of the advantageous features of the present invention, to integrate measurement unit, more specifically a detector optode into a solenoid that induces weak oscillating electromagnetic fields, overcomes surprisingly the major obstacles as outlined above. In contrast to the commonly used EEG detection, the optical method NIR does not interfere with any stimulation or entrainment methods based on the use of electricity or electromagnetic fields. Therefore, entrainment and measurement run simultaneously in real time eliminating the need to interrupt the process or trying to compensate cross talk mathematically, thus allowing the present invention being to be more robust, efficient, easy to operate and more economical. Furthermore, the device according to the present invention enables the measurement of brain pattern directly after completing the training process. In addition to the mentioned advantage, hemoencephalography in general is less prone to movement artifacts then EEG, making it highly suitable for fitness and health clubs.

In a preferred embodiment, possible interference problems of the device according to the present invention, wherein the plurality of compound units further comprises second measurement units comprising ring electrodes for the detection of real time electrical signals, may be circumvented via software control. In case the magnetic coils operate at a defined frequency, EEG data should be acquired only during "pulse-off" phases of the pEMF coils. Therefore, the type of entrainment has to be defined as "pulsed square".

Besides inducing neural oscillations at specific frequencies, weak pulsed electromagnetic fields generated by the entrainment unit, surprisingly influence additional neurological and metabolic functions favorable for bio-cybernetically controlled brain training. Measurements have shown that cerebral blood flow increases significantly in an area near the point of entrainment. Experiments performed by the inventors strongly indicate that the increase of cerebral blood flow depends on the field strength applied beside other factors. Due to the neuro-vascular coupling effect brain functions at pre-defined points of entrainment will be activated and conditioned for a specific cognitive task. Conditions of the performed experiences are described in detail below for FIGS. 9 and 10.

The integration of the at least two components in one unit according to the invention, i.e. entrainment via weak pulsed electromagnetic fields plus the optical detection via hemoencephalography into one single unit keeps the measurement and entrainment point of the device at the same position on the scalp when applied to the head of a person, ensuring a high degree of reproducibility and effectivity.

The field strengths applied in the human brain interface device connected to the system is kept in the range of 1 to 20 micro Tesla and operates at a maximum applied field strength of 3 milli Tesla for a defined conditioning process used in one application as further described within the present invention. It has been proven that patterned magnetic fields even down to 1 micro Tesla are not significantly attenuated by the human skull (Persinger and Saroka, J. Electromagn. Anal, Appl. 2013, 5, 151-156). In contrast to rTMS (repetitive transcranial magnetic stimulation) usually operating at field strengths in the range of 1 to 2 Tesla, weak pulsed electromagnetic fields do neither force neurons to fire nor produce heat. The technology according to the invention is safe, smaller in size, less costly and easy to operate as compared to the above described prior art. These are prerequisites for the implementation of this method in a non-clinical environment.

The brain will mimic the oscillation frequency of magnetic pulses at a frequency range between 4 and 40 Hz, usually termed "FFR". What the clinically applied forms of TMS is concerned, pulses at a frequency above 4 Hz cannot be applied in a continuous fashion, without short-time interrupts. There are several safety aspects to be considered as described by regulatory bodies.

As already described above, the human brain interface device comprises a plurality of multiple compound units positioned at specified locations around the scalp surrounded by a defined number of small light emitting diodes (LEDs) arranged in a specific geometry. The LEDs emit light within an optical window of 550 to 1000 nm. In one configuration the detector consists of frequency encoded laser diodes.

In a preferred embodiment, the measurement unit is a detector optode and the entrainment unit is a solenoid integrated in a housing with a defined number of small light emitting diodes (LEDs) arranged in a specific geometry.

In one further embodiment of the present invention, the multiple compound units are arranged in a physical matrix around the scalp following the international 10/20 standard for EEG electrode positioning, thus enabling the comparison of literature brain activation maps accessible from the database used by the system controlled by the method with the values measured in real time. The positioning geometry especially designed for EEG measurement has its merits in an optical measurement as well, since the neuro-vascular coupling mechanism synchronizes an elevated electrical potential with an increase in metabolic activities that is measurable by means of hemoencephalography. The 10/20 arrangement of the multiple compound units do further have the advantage of being complaint with external EEG databases.

In a further preferred embodiment, the compound unit comprises further a second measurement unit comprising ring electrodes for the detection of real time electrical signals.

Accordingly, the device according to the invention comprises the addition of EEG ring electrodes covering the solenoids for electroencephalographic measurement, thus having the advantage of providing a triple functionality integrated into one single unit.

This embodiment has the advantage that two independent measurement signal methods wherein the ring electrodes detect EEG signals and the integrated optodes generate complementary optical signals, wherein in one configuration of the device, the multiple compound units 503 are preferably arranged in a matrix or synonymously an array-matrix 502. In one further embodiment, this matrix comprises 19/22 active stimulation/measurement points according to the international 10/20 system. In another embodiment according to the invention, the matrix is an array matrix 602 with a reduced number of 7 multiple compound units 603 and 7 LED assemblies 604 located in the frontal area of the scalp complemented by 2 additional EMF solenoids 605 located at the back making the system scalable towards different user requirements.

To ensure an accurate, reproducible and safe positioning, each individual multiple compound unit comprises further an electro-magnetic functional unit in a cylindrical geometry made from metal with an inside cavity. A detector optode is located inside each cavity based on fiber optics in one embodiment. An inserted mechanism retains the first measurement unit, i.e. the detector in a defined position and applies the pressure required to enforce skin contact at the tip of the detector component. In one embodiment, this mechanism is essentially based on a loaded spring.

The housing of the device according to the invention comprises an inner layer and an outer layer, wherein the outer layer is made of a magnetic shielding material. This material may for example comprise in a preferred embodiment a copper/polyester blend.

The plurality of multiple compound units are mounted on a self-adjusting cap with holes at the defined positions of the matrix which forms the inner layer. The self-adjusting cap adapts to various head sizes in order to ensure the right contact and distance on the scalp.

The entire Human Brain Interface (HBI) Device has therefore a double layer format with the self-adjusting cap on the inside, the multiple compound units and cables in the middle all covered by the outer layer. In one embodiment of the device an electronic module 508 functioning as an amplifier, an A/D converter, a signal modulator and wireless transmitter and will be mounted between the layers enabling the device to function and communicate directly and wireless within the system, making the need of hardwiring the human subject to the system obsolete.

The outer layer of the device has a neutral and flexible surface, suitable for customization by third parties for commercial purposes and is made of a magnetic shield material, avoiding that the multiple compound units inside interfere with environmental electromagnetic radiation. This is specifically important in the case of weak pulsed electromagnetic as used in the present invention, since the applied magnetic field strengths are in a similar range (between 1 and 20 micro Tesla) as commercial communication devices such as mobile phones and other electronic household items emit today.

The problem underlying the invention is further solved by a brain entrainment system comprising the human brain interface device as described above and a control and/or processing unit which comprises means for:
controlling devices;
acquiring real time signals;
processing, transferring and/or receiving data to and from devices and databases;
and an output device.

The output device is preferably a content output device providing feedback to the human subject.

Specifically, the system according to the invention comprises the following means or in other words functional modules:

One Human Brain Interface device according to the first aspect of the present invention 201, a functional control and processing unit 202 including but not limited to functions of: controlling devices, acquiring signals in real time, processing, transferring and receiving data to other devices and databases, a database 203 storing and retrieving user specific personal and/or functional data, parameter sets, results and instrument log files, exchanging data with other databases and a content output device 204 providing feedback to the human subject.

In a preferred embodiment, the system according to the invention comprises the device according to the invention where multiple compound units are arranged in an array-matrix of 19/22 active entrainment/measurement points according to the international 10/20 system.

Another embodiment of the system comprises an embodiment of the device according to the invention wherein the following functional units are present: an array matrix 602 with a reduced number of 7 multiple compound units 603 and 7 LED assemblies 604 located in the frontal area of the scalp complemented by 2 additional solenoids 605 located at the back.

In still another preferred embodiment, the system 300 comprises an embodiment of the Human Brain Interface (HBI) device 301 wherein the following functional unit is present: an integrated electronic component, functioning—but not exclusively—as an amplifier, an A/D converter, a signal modulator and a wireless communication module for home based or mobile use. The Device (HBI) 301 communicates with the functional control and processing unit 302 running on mobile and/or desktop-based computing devices, while in another preferred embodiment, the mobile device is integrated with or connected to a virtual, augmented or mixed reality device combining the functional control and processing unit into one piece of hardware 402+404. In the integrated or connected piece of hardware the function to exchange data sets with a cloud-based server type 403 is present.

The measurement signals and output parameters are cybernetically controlled in real-time. The base function receives signals from the devices which are of optical nature in one embodiment; both electrical and optical in another embodiment, is processing the signals, generating output data in at least two ways:

Cybernetically controlled means in the context of the present invention namely: (a) output data transferred to the device in a code that generates specific and parameterized pulsed electromagnetic fields and (b) output parameters controlling the content output device to the human subject. Control parameters of the pulsed electromagnetic fields that are important in the context of the present invention are: (e1) Oscillation frequency of the electromagnetic field, (e2) type of entrainment curve, (e3) magnetic field strength and (e4) phase of the entrainment curve in respect to different locations within the array matrix of the multiple compound units. Of high interest are specific entrainment curves wherein the magnetic field strength alters periodically as a function of time. Applying this technical feature, communication patterns of dedicated brain structures will be simulated enabling an even more dedicated training of cognitive and emotional brain functions.

In one embodiment of the system output parameters for controlling the multiple compound units of the device generate electromagnetic fields ranging from 0 to 3 milli Tesla and pulses between 1 and 150 Hz at different entrainment waveforms and phase settings between individual multiple compound units.

The data base (203; 303; 403) of the system retrieves, sorts, stores, processes and secures user specific data amongst others. User specific data contain one or more but are not limited to following elements: personal data, training methods associated with optical brain activation maps complemented by QEEG data in another embodiment, stimulation parameter sets session history log, training results and calculations comprising on or more of the mentioned parameters. Personal data include preference and safety parameters enabling to adjust and personalize feedback environments among others. Feedback devices comprise of one or more of the following elements: Virtual and augmented reality devices, tactile feedback devices, instruments providing visual and auditive feedback via googles, monitors, real and heads-up displays, olfactory output devices and simulation hardware.

The term "simulation hardware" categorizes all external devices connected to the system as an "output" device receiving processed or unprocessed data from the software-based functional unit of the system and alter their mode of operation based on the data received.

In one specific embodiment, the simulation hardware is a training machine for physical fitness.

In one further preferred embodiment of the system, the software-based functional unit is on a wireless mobile computing device and the communication between the device, the content output device and the mobile computing device is wireless, thus allowing the operation of the system in a sport/fitness facility, where the human subject is in motion. As mentioned, movement artefacts are present to a much lesser extent when hemoencephalograpy is used to monitor dynamic changes in brain activities compared to using an electrical detection method of brain activities such as electroencephalography. As measurements show, intensive motion of the human subject has even the effect to slightly decrease the levels of blood oxygenation in the prefrontal areas, as shown in FIG. 9, contrary to the observed increase of blood oxygenation during executive cognitive tasks. This surprising outcome makes the system ideally suited for a completely wireless operation, opening new routes for a cognitive training of humans while executing a both physically and mentally demanding task such as athletic sports.

The problem is still further solved by the use of a system according to the invention in a method for training and optimization of brain functions comprising the following steps:

calibrating the device according to any one of claims 1 to 4 by baseline measurements of multichannel hemoencephalographic brain patterns 801;

setting start entrainment and feedback output conditions 802 by loading the brain stimulation data matrix corresponding to a hemoencephalographic brain activation map from a database;

starting the entrainment and feedback program 803;

measuring the hemoencephalographic brain pattern 804;

comparing the actual measurement 805 of step d) with values from the database and/or dynamic changes of values within the continuous measurement;

adjusting entrainment parameters 806 according to the result of the comparison in step e) (Loop 1);

modifying feedback output 807 to the user based on the comparison in step e) (Loop 2) in a continuous dual closed loop until program end;

storing session log and results in the database 808.

The above-mentioned steps are based on bio-cybernetical regulation mechanisms controlled by intrinsic feedback loops. Workflows are designed to be processed by the system described in the present invention utilizing PC based and non-PC based computing systems including tablets and smart phones, a proprietary data base amongst the functionality to export and import data from $3^{rd}$ party and public data bases and the option to store data in a cloud.

The major advantage of using two feedback loops based on the comparison of measured data with optimized data is the following:

The intrinsic feedback loop according to step g) modifies the feedback output presented to the human subject based on instant dynamic changes that occur in the human brain detected by the array of multiple compound units in real time. Modifications of the feedback are either sending reward or neglect signals to the human brain based on the result of the comparison according to step e), thus inducing a self-regulation process of the human subject each time the output feedback modifies presenting the human brain a reward or neglect signal. The feedback loop according to step f) surprisingly acts as a "pace maker" for the human brain by activating selective brain regions. As mentioned in the present invention the said activation happens in two ways: (1) increase of cerebral blood flow in the brain regions entrained, (2) entrainment of oscillation frequencies defined by the pulse rate of the electromagnetic fields applied. The "pace maker" function controlled in a closed feedback loop according to step f) has an important function especially in a non-clinical environment, when human subjects are engaged in their daily processes, often stressed and/or loaded with mental chatter. By means of applying step f) the threshold of focus and concentration needed to make g) an effective process will be achieved in a personalized and training task specific way and further ensures that the focus will last for the entire training session ahead. Another big advantage of step f) being present in said method is that the process herein described as "pace making" runs fully automatically thus the operator of said method does not need any knowledge about the status of the human subject nor the underlying mechanism. The training effect will be maximized independent from the pre-deposition of the human subject resulting on a wider applicability of the method with a higher success rate and faster protocols.

Preferably, the start entrainment condition of step b) contains at least one of user specific data comprising personalized output parameters, brain activation maps and/or corresponding entrainment parameters.

The initial parameter-sets downloaded 705 from the data base in step b) contain user specific data, containing personalized feedback configuration parameters, brain activation maps and corresponding entrainment parameters corresponding to the so far best training results. The data sets contain personalized feedback configuration parameters, brain activation maps and the corresponding stimulation parameters. This step ensures a high degree of personalization. Human subjects build up on the best results they achieved within a specific training under defined conditions, therefore repetitions of the method as part of a regular training program consisting of multiple sessions, will be more effective and the desired results achieved in a shorter time period.

The method is embedded in two categories of applications. Each application category contains executable applications defined in SOPs. Each SOP defines the process and data flow amongst other parameters. Each application further comprises step a) to step h) according to the method. The method further comprises the use of means for feedback control.

Other embodiments of the method according to the invention can be summarized under the category "Cognitive Enhancement and Stress Resilience" 701 (CESAR) and comprise pre-defined processes designed for sport and recreational facilities, keeping down the cost and complexity for business owners and their staff. Within said method variation, following program routines 701 are activated before the starting step. The Calibration/Baseline setting 703, executing the following: guide the operator through SOPs containing instructions for each manual step and loading pre-configured training programs. As a result, the Method becomes accessible for operators in sport and recreational environments outside medical centers. The workflows are compatible with all embodiments of the system disclosed in the present invention amongst others, are pre-defined for, but not limited to, brain training programs as follows: Cognitive Enhancement, Stress Resilience, Fast and Deep Relaxation.

Other embodiments of the method according to the invention can be summarized under the category "Neuroadaptive Skill Training & Prevention of Cognitive Decline" 702 (NADPO) alter and optimize brain functions in a specific and targeted way enabling an effective training of human subjects with either a (Case 1) pre-deposition, for example elderly people showing a mild cognitive impairment, or (Case 2) business and sport professionals to improve and optimize specific skills.

Regarding Case 1, "Prevention of Cognitive Decline", the method addresses a specific training of memory and the improvement of spatial/temporal orientation amongst others and contains a pre- and post-conditioning sequence of operations embedding the method executes following steps: i) stimulation of defined cortical areas by applying a pulsed electromagnetic field with a defined parameter set leading to a metabolic activation of the respective cortical areas, ii) running a stimulation program strengthening long distance brain network hubs, iii) activating defined brain regions by applying an oscillation frequency similar to the typical neural oscillation pattern; defined brain regions are the once usually affected at 1st in case of mild cognitive impairments The method according to the invention further comprises the following steps of:
applying interhemispheric-offset stimulation, wherein the oscillation profile applied to the multiple compound units arranged in the matrix at positions 1, 3, 5, 7, 9 are out of phase with those arranged in the matrix at positions 2, 4, 6, 8, 10; and/or random noise stimulation;
applying a defined frequency, wherein the oscillation profile applied to the multiple compound units arranged in the matrix at positions 1, 3, 5, 7, 9 are in phase with those arranged in the matrix at positions 2, 4, 6, 8, 10;
applying a specific oscillation frequency for a selected position of a compound unit arranged in the matrix.

Regarding Case 2 "Neuroadaptive Skill Training", the methods are composed to improve the overall performance in a defined sequence of specific tasks needed for mastering mentally demanding sports wherein the human subject has to process multi-sensory input information, coordinating and executing complex motion tasks, and executive decisions, within a minimum time period, often under physical and mental stress. Therefore, in Case 2 "Neuroadaptive skill training", a sequence of operations is present, embedding the method and comprising following steps: i) Applying interhemispheric-offset stimulation whereby the oscillation profile applied to the multiple compound units on the left side are out of phase with those on the right side and/or random noise stimulation. Applying this step, the brain of the human subject receives irregular signals that cannot be interpreted and processed the regular way, consequently human subjects will be "dis-entrained" from mental chatter and stress; j) Entrainment of anterior and posterior positions of the multiple compound unit matrix by applying a defined frequency whereas the oscillation profile of said positions are in phase, will lead to a coherent communication between long distance network hubs within the brain, strengthening the effectiveness of integrating processed information, k) activate pre-defined brain regions by applying a specific oscillation frequency for selected positions of the multiple compound unit matrix. Human subjects performing different cognitive tasks show specific neural communication activities underlying certain oscillation patterns of electrical signals as well as an enhanced metabolic activation of brain areas involved in the task. Applying step (c) as described herein utilizing the system has a synergistic effect: entrainment of specific brain frequencies at defined positions within the area-matrix of the multiple compound units where the brain gets into resonance coupled with a metabolic activation by means of the weak pulsed electromagnetic fields induced, thus making the conditioning more effective and target specific leading to a faster and better brain performance for the task ahead.

The feedback output in step g) is preferably a VR/AR simulation comprising one or more of the following training scenarios: team sports, individual competitive sports, business and professional activities, interactions between two or more human subjects.

Thus, the feedback output in step g) is a VR/AR simulation, facilitating a neuroadaptive simulation training of various sports and business professional activities. VR/AR simulations set the human subject in an immersive environment facilitating a training close to reality. The higher the immersion of the human subject, the deeper the brain gets involved leading to better training effects with more profund adaptations in neural communication and inter-synaptic connections, leading to a higher sustainability of the brain optimization. The said method enables mental performance training in sports or business environments simulating original locations, such as characteristics of existing Golf Courts in VR or AR mode. Today VR Golf Simulators are existing, however making such environments neuro-adaptive is a major innovative step. Feedback control routines are designed to give reward/non-reward signals to the human subject, in the form of visual, auditory, olfactory and tactile feedback, alter immersive environments, control video games, real objects and VR/AR simulations.

In a preferred embodiment the feedback output comprises a recorded movie or scene consisting of a 360° C. 3D or Virtual Reality format, wherein the recorded movie or scene is modified in step g).

Thus, the initial parameter-sets downloaded 705 from the data base in step b), comprises a recorded movie or scene in, but not limited to, a 360-degree 3D or Virtual Reality format and the said recorded movie or scene is modified in step g), enables the human subject to recall and retrain their past scenarios recording the neural trace within the specific tasks linking brain activation patterns to the actual performance in a chronological way.

In another embodiment of the invention, a program extension recalls step b) and stores personalized datasets in step h) including task-optimized brain stimulation parameters remotely from a real or cloud-based database to a computing device, wherein the computing device is a personal computer or a mobile device.

Among the data sets task optimized brain entrainment parameters and hemoencephalographic brain maps are compared with the actual feedback task performance on a time scale over the course of the simulation. Thus, enables a retrospective neuroadaptive reconstruction of the entire simulation and determine where the weak and strong points are in the simulation and what the brain actually does at this point. This procedure allows a specific neuroadaptive optimization of a human subject in motion, performing in one scenario a VR/AR golf simulation where the exact movements are carried out as in reality. One method variation in this respect is that step (g) of the method is carried out in augmented reality, wherein the operator and the user are the same person.

In a specific embodiment of the invention, the feedback output in step g) is directed to and executed by a training machine for physical fitness presented to the human subject based on the dynamic changes measured in the previous step in a continuous dual closed loop until program end, combines the synergies between physical and mental fitness training.

It has been proven that an aerobic exercise has a positive effect on cognitive capabilities for different reasons. Latest research even reports synergistic effects when training brain and cardiological functions simultaneously.

A further advantage of integrating brain and body fitness training is a time saving for both the trainee and the trainer.

BRIEF DESCRIPTION OF THE DRAWINGS

The invention is described in more detail by way of the following figures and explanations thereto which show certain embodiments of the invention without being meant to be limiting for the scope of the invention.

DETAILED DESCRIPTION

Figure 1:
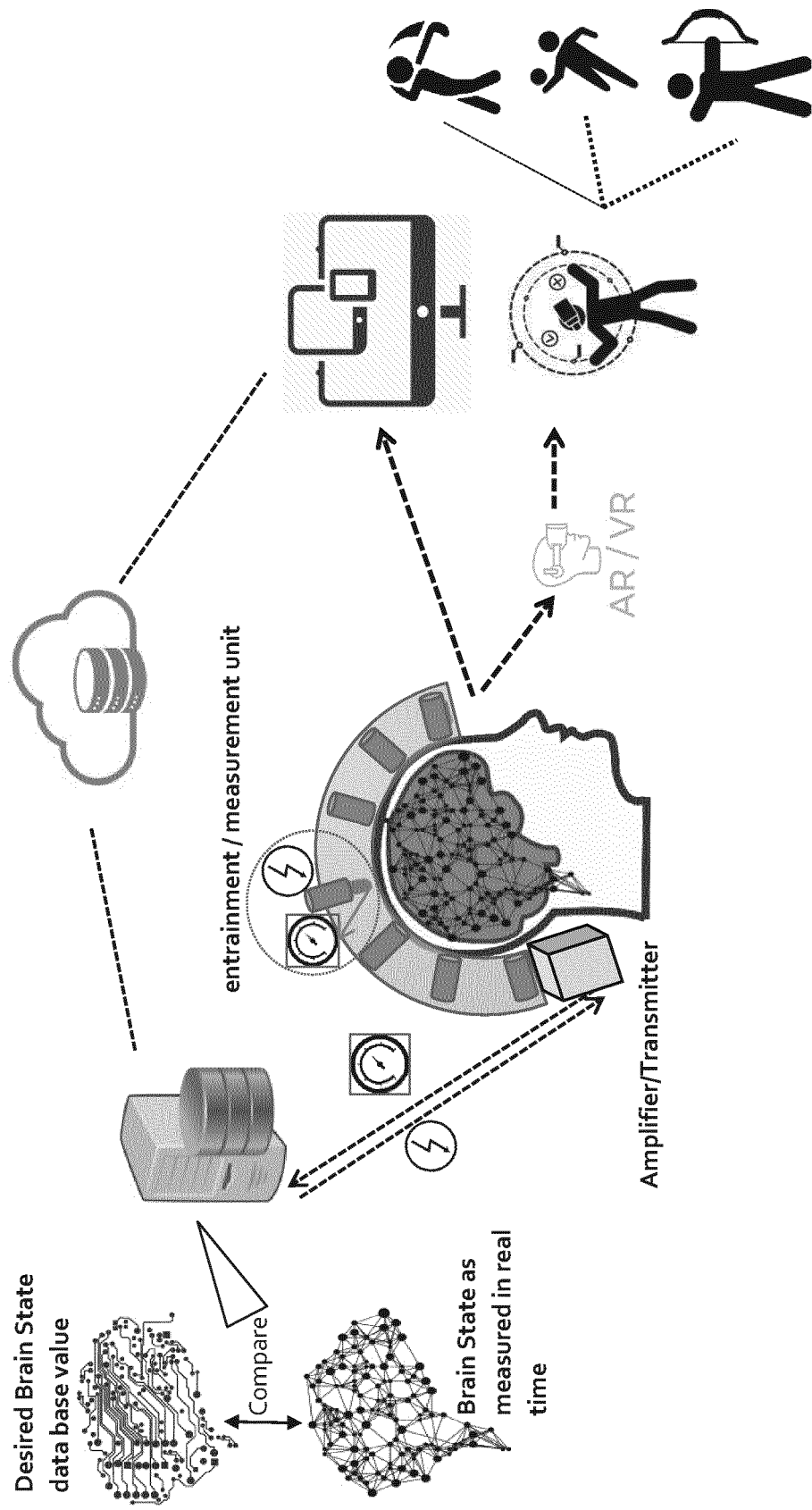
FIG. 1 shows a schematic representation of the system according to the invention comprising a device of the invention

FIG. 1 shows a schematic representation of the system according to the invention comprising a human brain interface device of the invention, comprising multiple compound units, whereas brain entrainment/non-invasive brain stimulation functionalities and functionalities for brain activity measurement are present. The system further comprises of a functional control and processing unit, whereas the function of comparing brain states measured in real-time with desired brain states obtained from a database is present; a database, whereas the data base is—but not exclusively cloud-based; a content output device providing feedback to the human subject, whereas the content output device comprises monitors, tablets, smart phones and virtual/augmented reality devices. Feedback output content comprises of movies, video games, simulations in virtual and augmented reality, whereas simulations comprise of training scenarios for different kind of sports amongst others.

Figure 2:
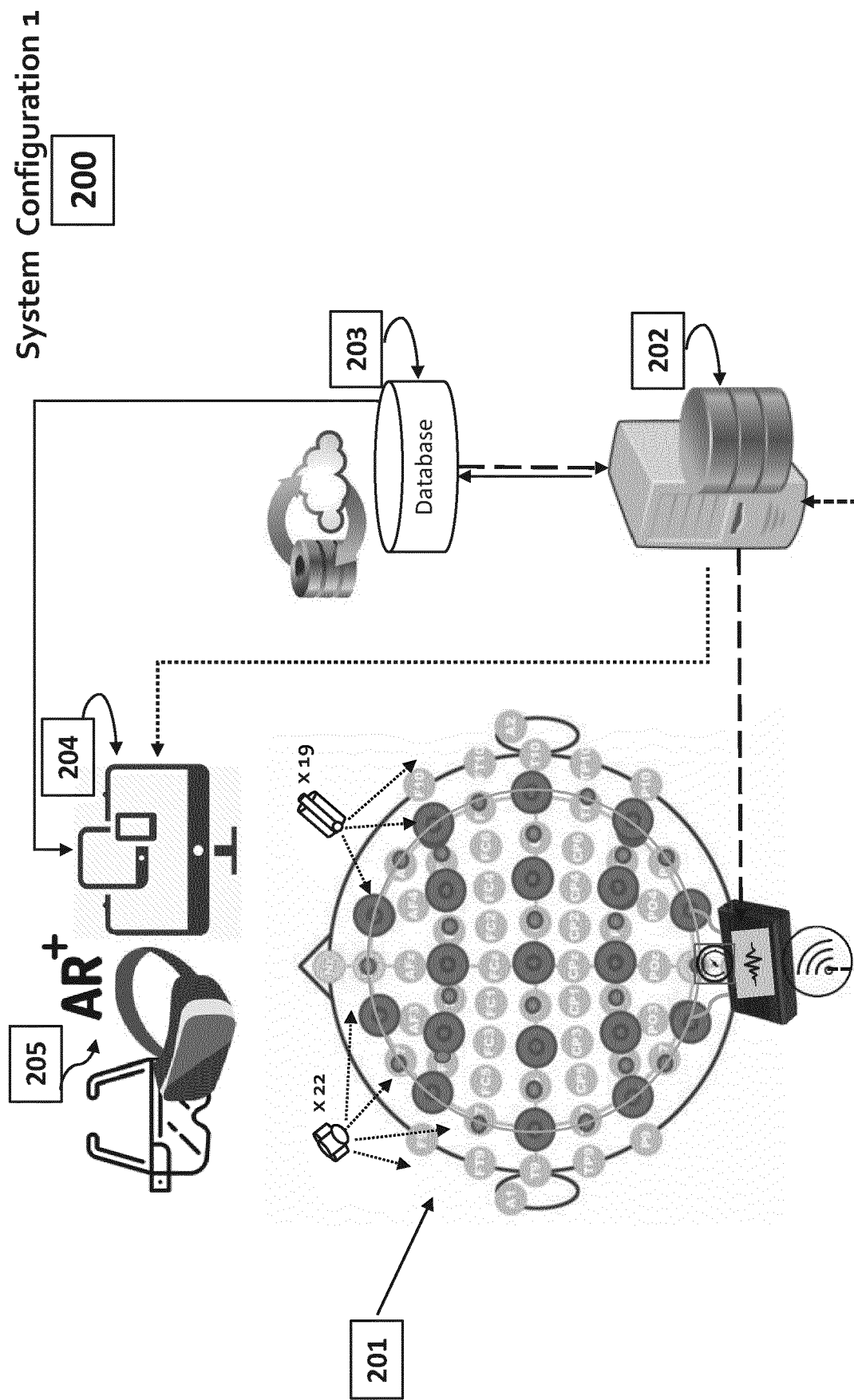
FIG. 2 shows a first embodiment of the system according to the invention

FIG. 2 shows a first embodiment of the system according to the invention 200 which is also termed as configuration 1. This first embodiment has the following components: A human brain interface device according to the present invention 201, a functional control and processing unit 202, whereas functions include: controlling devices, acquiring signals in real time, processing, transferring and receiving data to other device and databases, a database 203, whereas the database is—but not exclusively—cloud-based and a content output device 204, providing feedback to the human subject, whereas the content out device comprises a VR/AR device 205, in one embodiment.

Figure 3:
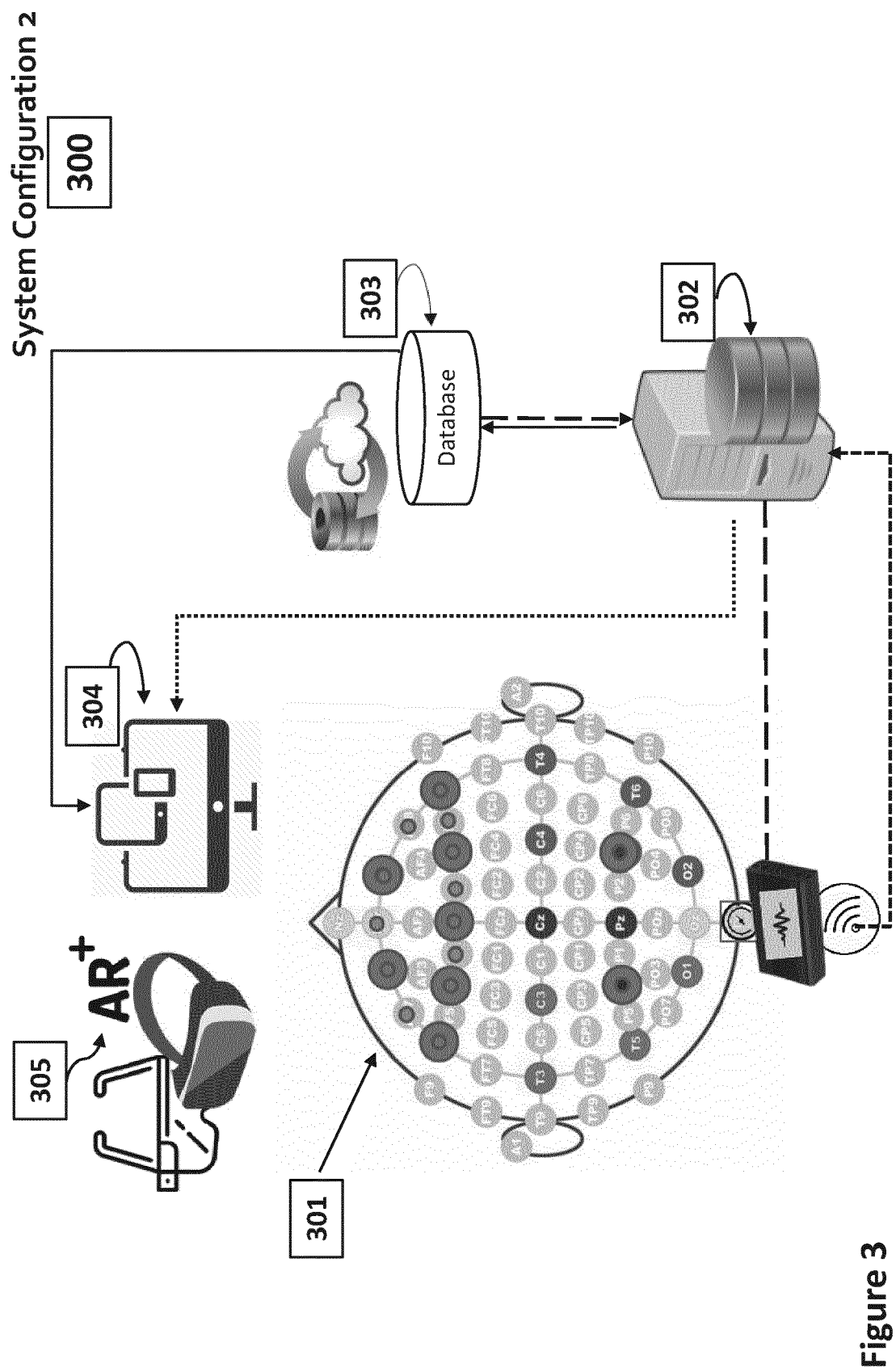
FIG. 3 shows a second embodiment of the system according to the invention

FIG. 3 shows a second embodiment of the system according to the invention 300 also termed as configuration 2. In this embodiment the system 300 comprises an embodiment of the Human Brain Interface (HBI) device 301 wherein following functional unit is present: an integrated electronic component, functioning—but not exclusively—as an amplifier, an A/D converter, a signal modulator and a wireless communication module for home based or mobile use. The Device (HBI) 301 communicates with the functional control and processing unit 302 running on mobile and/or desktop-based computing devices and controls the content output device 304, that provides feedback to the human subject. The content output device 304 and the functional control and processing unit 302 are connected to a database 303 to exchange data sets. The content output devise comprises a VR/AR device in one embodiment 305.

Figure 4:
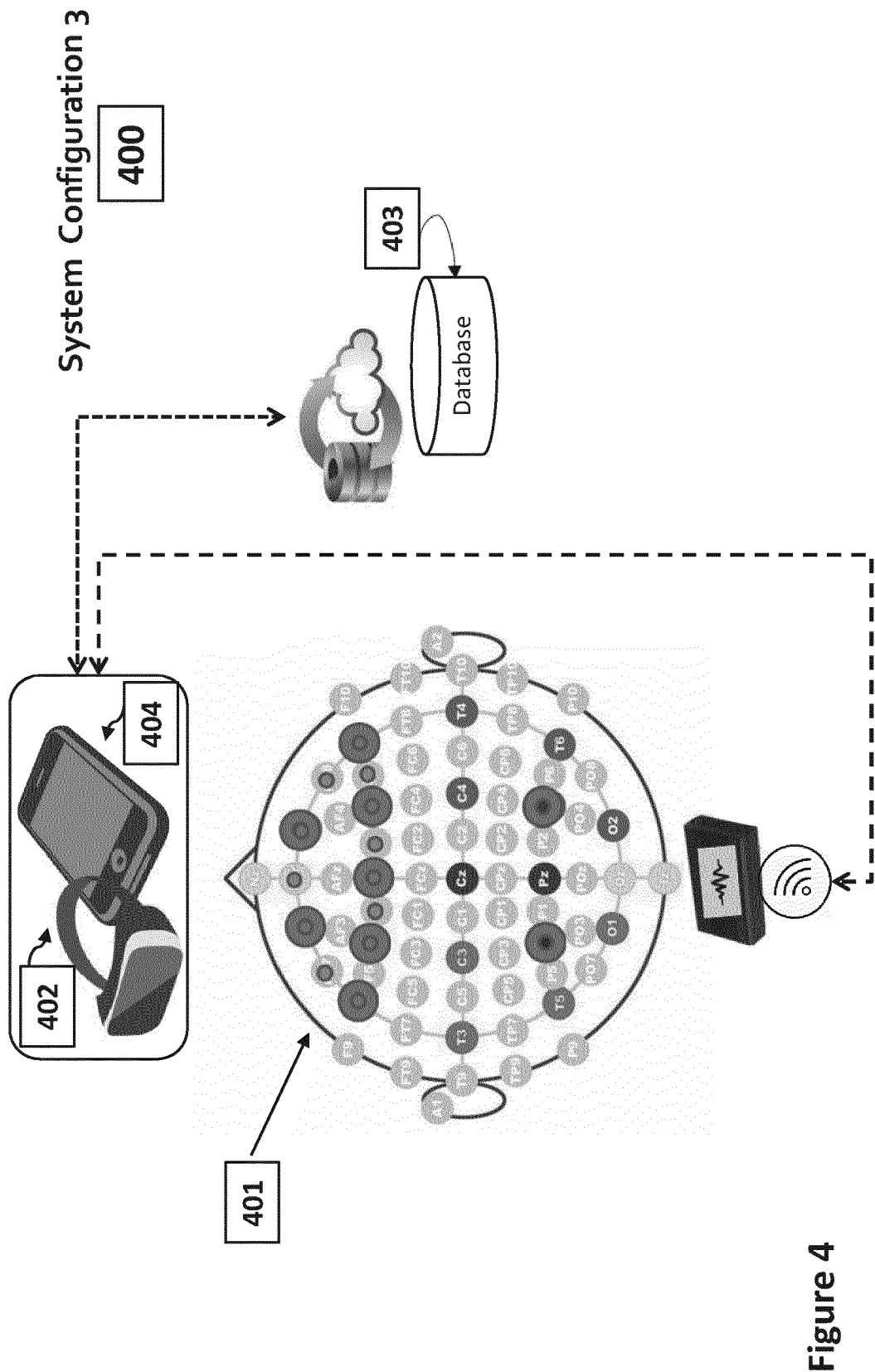
FIG. 4 shows a third embodiment of the system according to the invention

FIG. 4 shows a third embodiment of the system according to the invention 400 also termed as configuration 3. In this embodiment the system 400 comprises an embodiment of the Human Brain Interface (HBI) device 401 wherein following functional unit is present: an integrated electronic component, functioning—but not exclusively—as an amplifier, an A/D converter, a signal modulator and a wireless communication module for home based or mobile use. The Device (HBI) 401 communicates with the functional control and processing unit 402 running on mobile and/or desktop-based computing devices and controls the content output device 404, that provides feedback to the human subject. In another embodiment, the mobile device is integrated with or connected to a virtual, augmented or mixed reality device combining the functional control and processing unit into one piece of hardware 402+404. In this integrated or connected piece of hardware the function to exchange data sets with a cloud-based server type, i.e. a database 403 is present.

Figure 5:
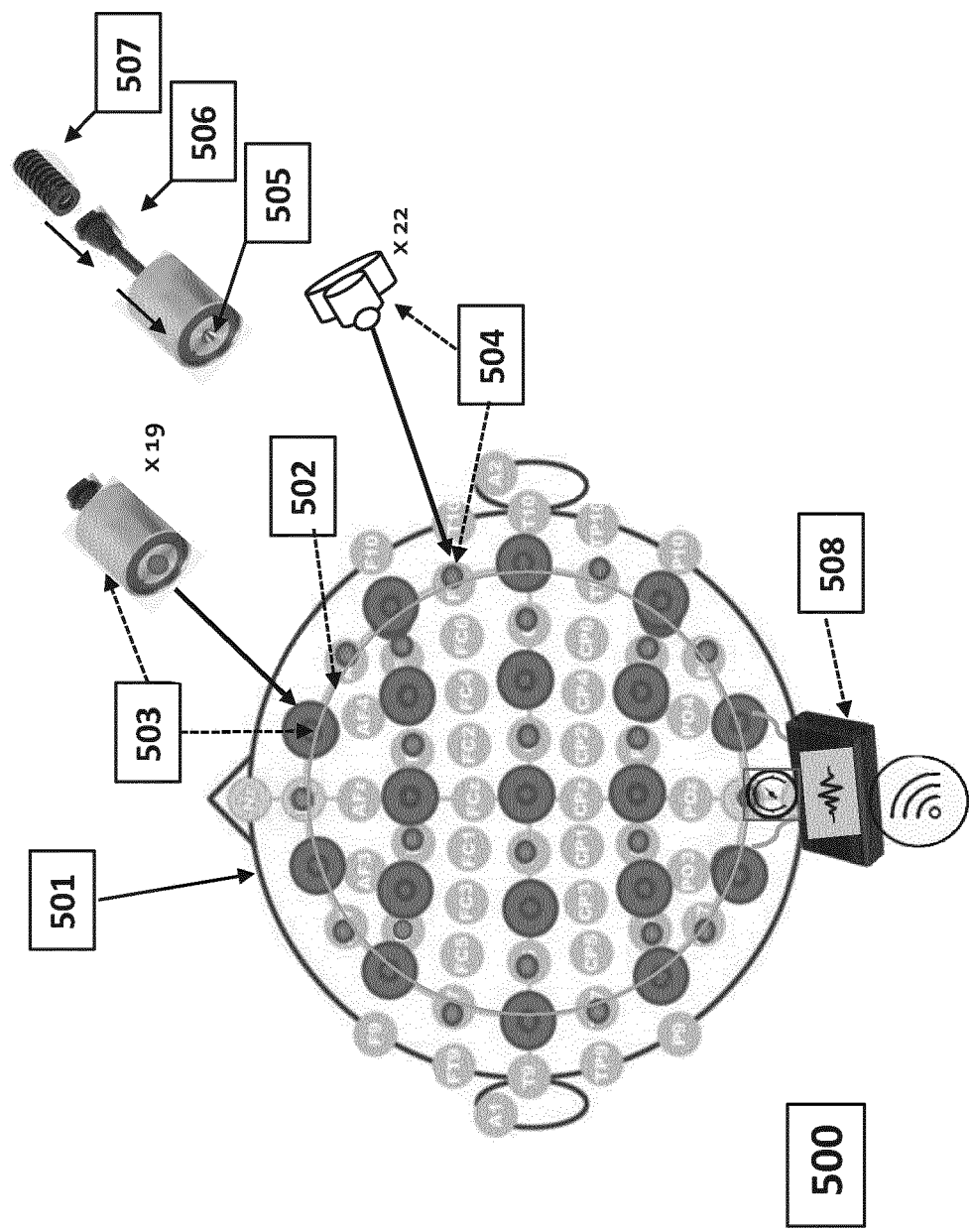
FIG. 5 shows a first embodiment of the matrix and functional components of a device according to the invention
Figure 6:
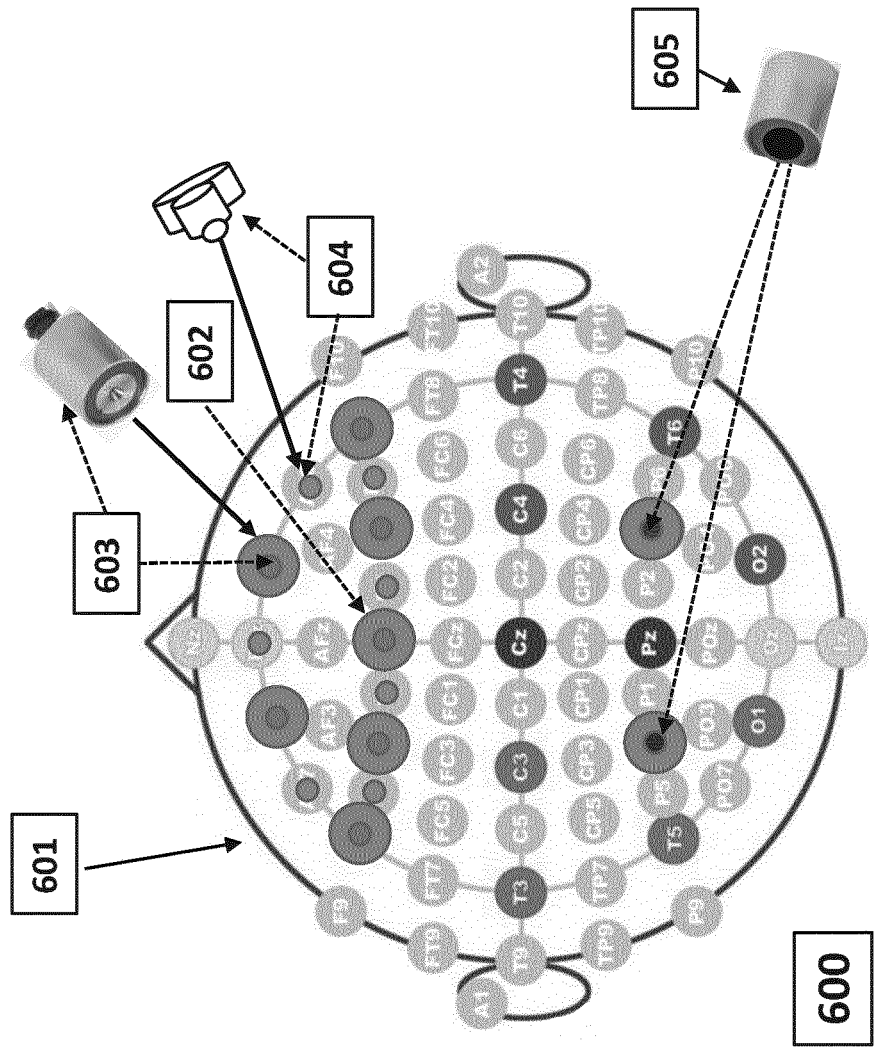
FIG. 6 shows a second embodiment of the matrix of a device according to the invention

FIG. 5 shows a first embodiment 500 of the functional components of the Human Brain Interface (HBI) device 501 according to the invention. In this configuration 19 multiple compound units 503 and 22 LED assemblies 504 are arranged in an array-matrix 502 of 19/22 active stimulation/measurement points according to the international 10/20 systems. The multiple compound units 503 comprise of an assembly of a cylindrical solenoid with an inside cavity 505, a detector optode based on fiber optics in a preferred configuration 506. In one configuration a spring-loaded mechanism 507 ensures good skin contact of the detector optode. LED assemblies may consist of 2 light emitting diodes covering the wavelength range between 550 to 1000 nm. Further, the device 501 comprises an electronic module 508 with wireless data transmission function FIG. 6 shows a second embodiment 600 of the functional components of the Human Brain Interface (HBI) device 601 according to the invention. In this configuration a reduced number of 7 multiple compound units 603 and 7 LED assemblies 604 are arranged in an array-matrix 602 in the frontal area of the scalp as shown, complemented by 2 additional EMF solenoids 605 located at the back making the device scalable towards different user requirements by utilizing different embodiments of the device.

Figure 7:
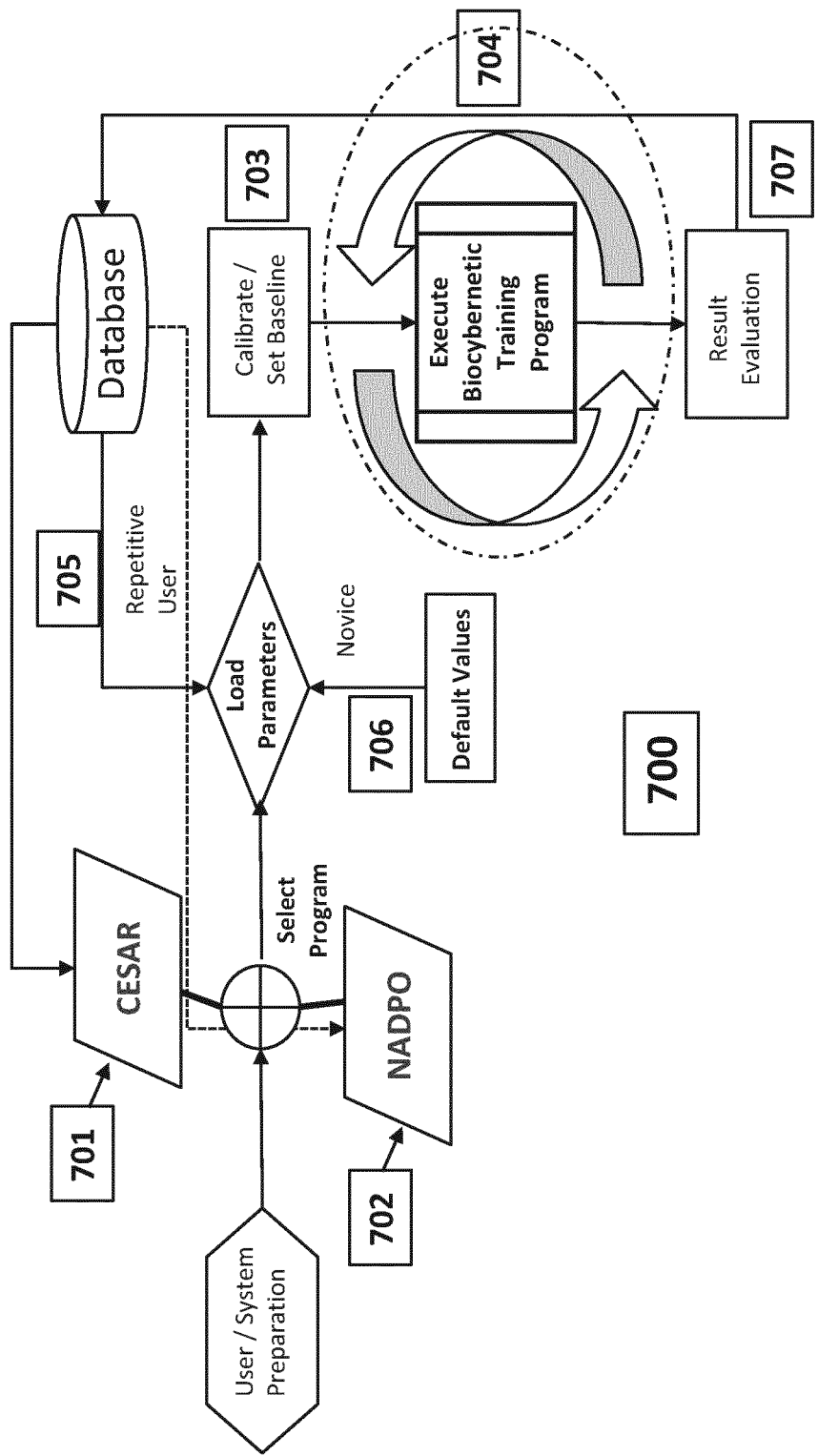
FIG. 7 shows an overview flow chart for the process used by the system according to the invention
Figure 8:
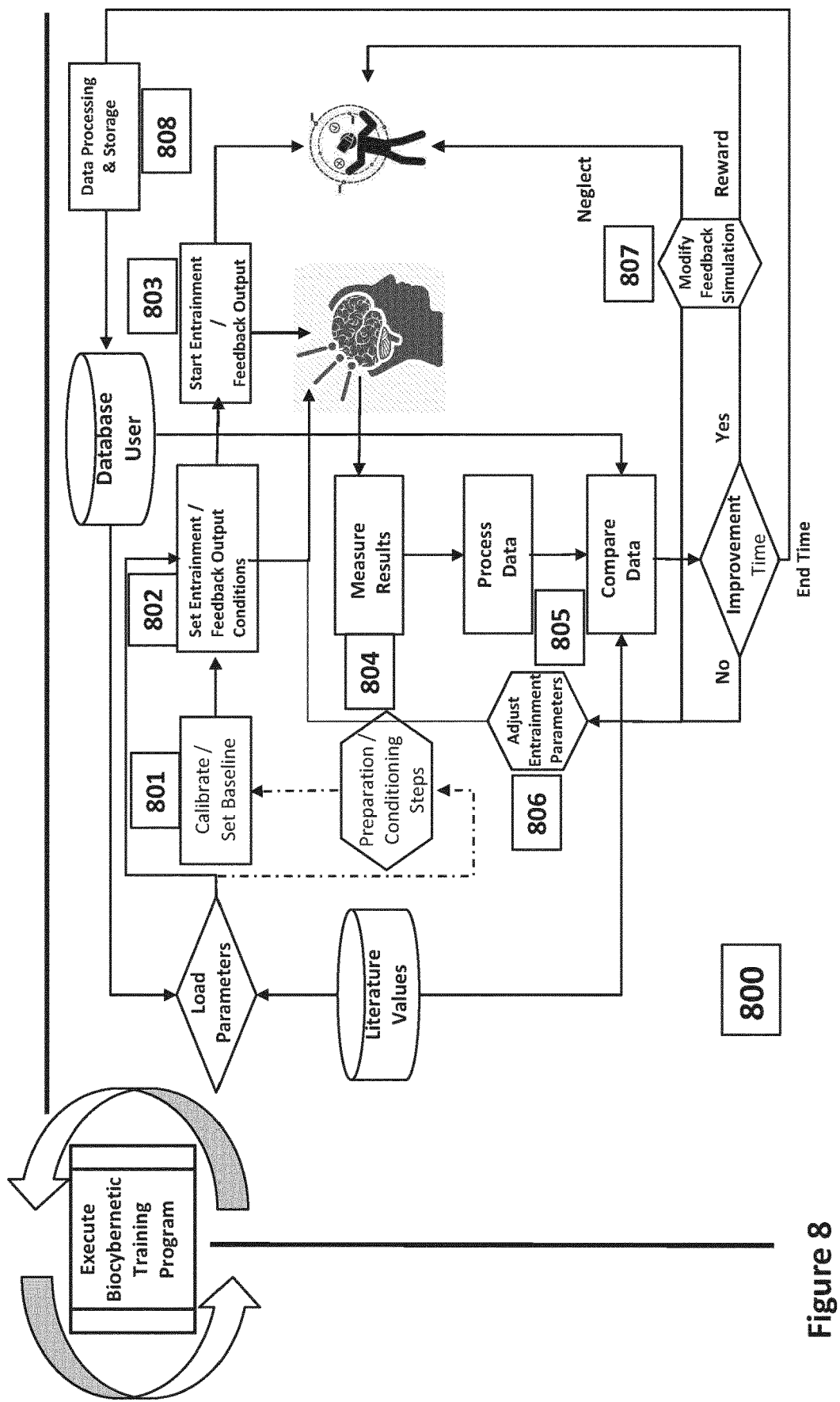
FIG. 8 shows a second flow chart for the central neuro-adaptive process used by the system according to the invention

FIG. 7 shows a on overview flow chart 700 for the process used by the system according to the invention. The process according to the invention is embedded in two categories of applications, CESAR 701 and NADPO 702 (see below). Each application category contains executable applications defined in SOPs. Each SOP defines the process and data flow amongst other parameters. Each application further comprises the bio cybernetically controlled process 704 as illustrated in FIG. 8 including step a) to step h) according to the said method. The method further comprises, result evaluation 707, whereas training results are evaluated in relation to the training parameters and of the human subjects as well as sensor readings as processed and stored in a database, allowing to start a repetitive training process for the same human subject under optimized parameters and entrainment conditions by downloaded user specific data (705), whereas for a human subject applying said method for the 1$^{st}$ time a default set of parameters will be downloaded (706) containing optimized parameters for the type of training selected.

Variations of said method summarized under the category "Cognitive Enhancement and Stress Resilience" 701 (CESAR) comprise pre-defined processes designed for sport and recreational facilities, keeping down the cost and complexity for business owners and their staff. Within said method variation, following program routines 701 are activated before starting step "The Calibration/Baseline setting 703, executing the following: guide the operator through SOPs containing instructions for each manual step and loading pre-configured training programs. As a result, the Method becomes accessible for operators in sport and recreational environments outside medical centers. The workflows are compatible with all embodiments of the system disclosed in the present invention amongst others, are pre-defined for, but not limited to, brain training programs as follows: Cognitive Enhancement, Stress Resilience, Fast and Deep Relaxation.

Variations of this method summarized under the category "Neuroadaptive Skill Training & Prevention of Cognitive Decline" 702 (NADPO) alter and optimize brain functions in a specific and targeted way enabling an effective training of human subjects with either a (Case 1) pre-deposition, for example elderly people showing a mild cognitive impairment, or (Case 2) business and sport professionals to improve and optimize specific skills FIG. 8 shows a second flow chart 800 for the for the central neuroadaptive process used by the system according to the invention. The process (or method) comprises the following steps and may comprise further steps for pre- and/or post-conditioning of the human subject. 801 Calibration by baseline measurement of multichannel hemoencephalographic brain patterns utilizing the System described herein. Set entrainment and feedback output conditions 802 by loading the brain stimulation data matrix corresponding to the hemoencephalographic brain activation map and the human subject specific feedback parameters from the database as shown in FIG. 7. 803 Start the entrainment and feedback program. 804 Measurement of the hemoencephalographic brain pattern. 805 comparing the actual measurement with values from the data base and/or dynamic changes of values within the continuous measurement. 806 Adjust entrainment parameters as a result of the comparison executed in the previous step (Loop 1). 807 modify feedback output presented to the human subject based on the dynamic changes measured in the previous step (Loop 2) in a continuous dual closed loop until program end. 808 store session log and results in the database.

Figure 9:
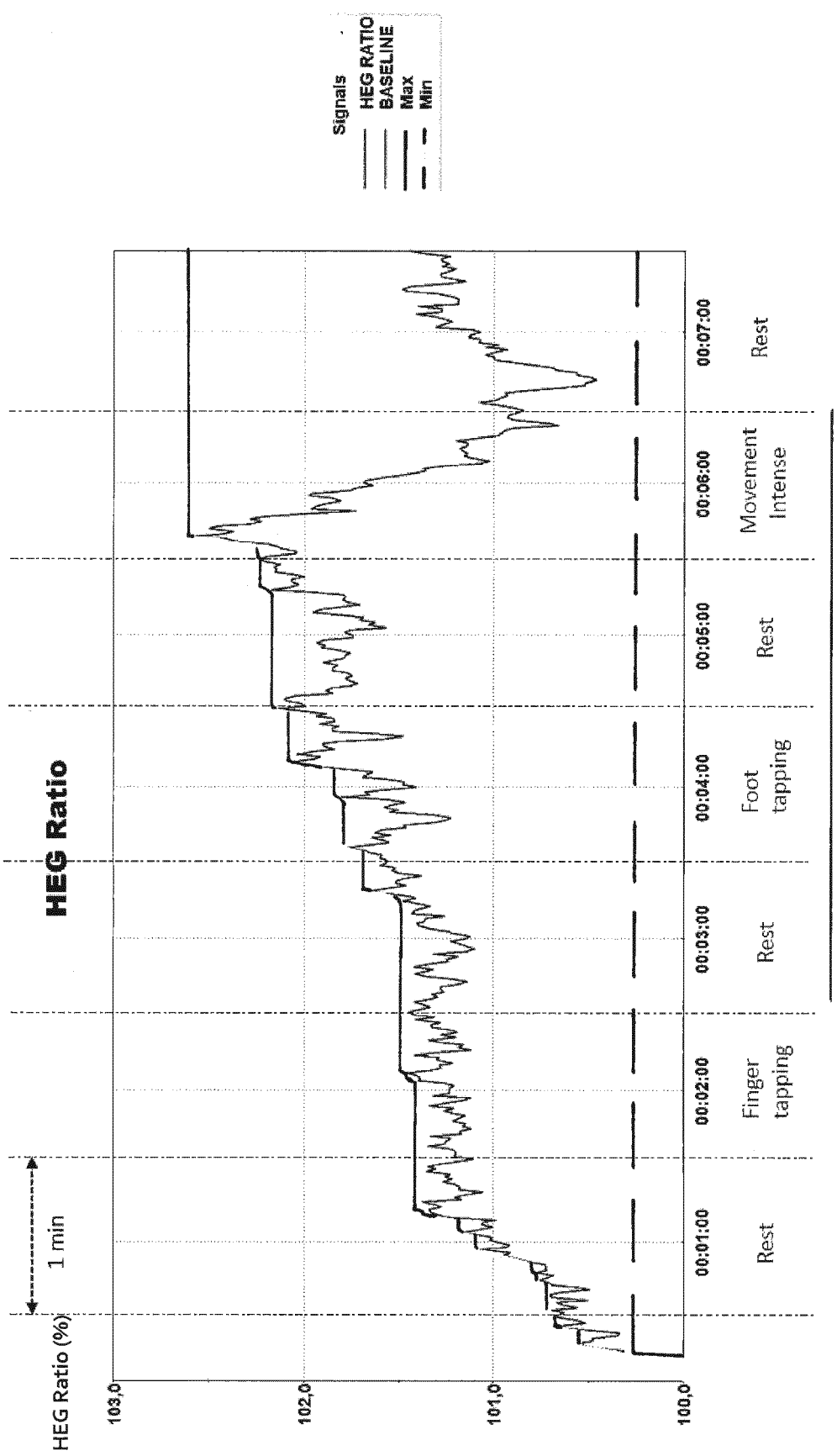
FIG. 9 shows a first hemoencephalogram measuring the influences of movements of the human subjects on the baseline

FIG. 9 shows a first hemoencephalogram measuring the influences of movements of the human subjects on the baseline. The experiment started by calibrating the baseline to a HEG ratio value of "100" with the human subject resting in a chair. HEG ratio measured showed a value of "101", meaning an increase of 1% of the baseline after the human subject remained 1 min at rest. Tapping with the fingers for another minute did not how an increase of the HEG ratio value. After another resting period of 1 min the human subject performed a tapping movement with both feet. The HEG ratio value increased by circa another 0.75% and remained at a value between "101.5" and "102" after another minute at rest. The $3^{rd}$ movement carried out by the human subject at time scale t=5 min was an intense uncoordinated movement with both arms and legs. The said movement activity let the HEG ratio value drop near the baseline between "100" and "101" at t=6 min. The experiment shows that movements of the human subject do not influence the HEG ratio value significantly. Since HEG ratio gains applying said braining training method are usually in the range of 10%, movement artefacts play a minor role applying said method.

Instrumentation: NIR Sensor: HEG Headband, Se-No. P5597, supplier Biocomp Research Institue 2525 Sawtelle BI Los Angeles, CA 9006; measurement point of the pre-frontal cortex Fp1; Hardware Electronics: Q-Wiz, Se. No 798768, supplier Pocket Neurobics, 12 Corgen Ave. Terrey Hills, NSW 2084 Australia; Software: BioExplorer Version 1.6 v1.7.0.661, Supplier "CyberEvolution Inc."

Location of measurement: pre-frontal cortex Fp1; The parameter HEG value is determined by a mathematical calculation and indicates the ratio of oxygenated to non-oxygenated hemoglobin in the cerebral blood.

Figure 10:
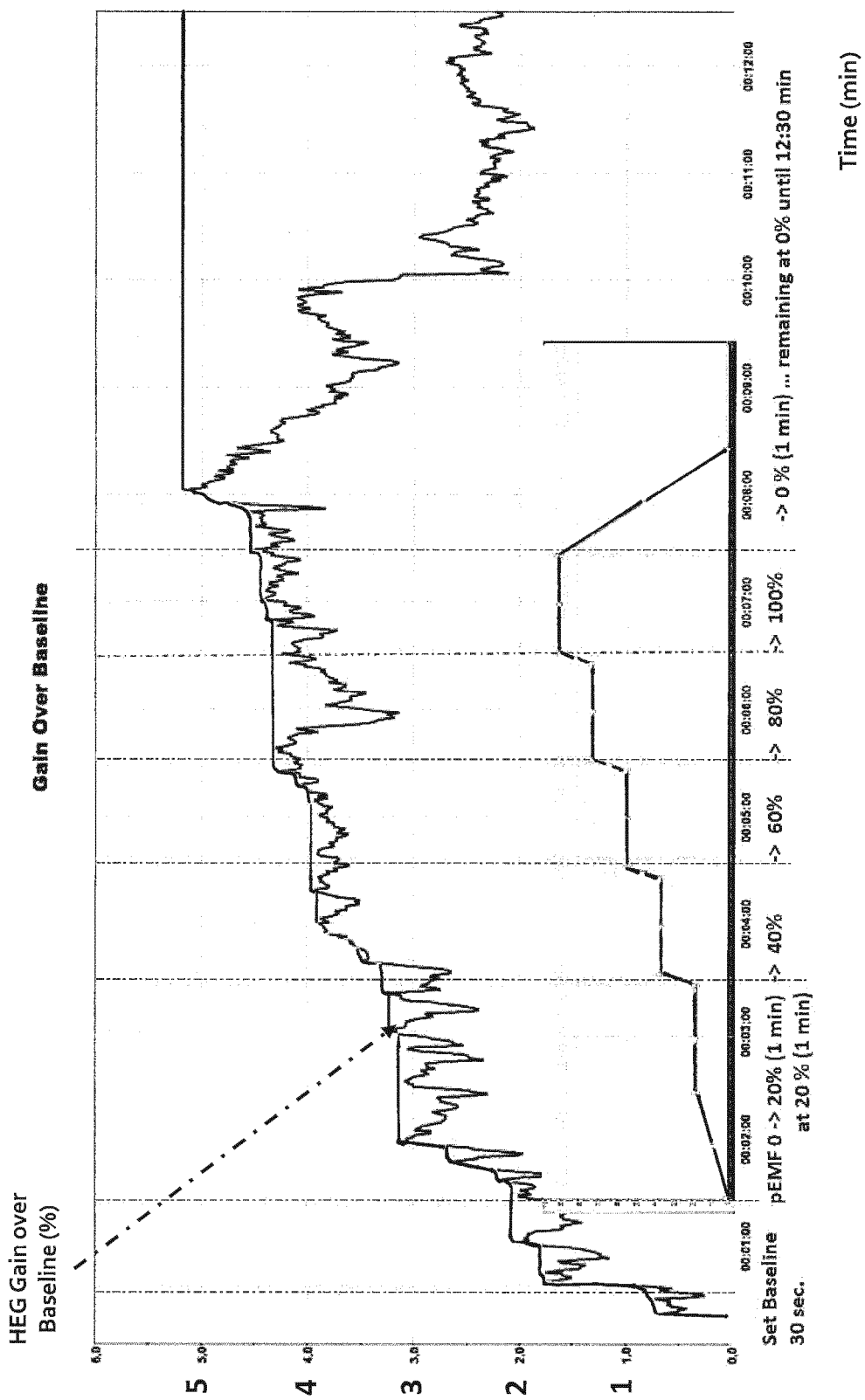
FIG. 10 shows a second hemoencephalogram measuring the influence of pulsed electromagnetic fields on the cerebral blood flow near the stimulated brain areas

FIG. 10 shows a second hemoencephalogram measuring the influence of pulsed electromagnetic fields on the cerebral blood flow near the stimulated brain areas. During the experiment the human subject did rest on a chair with eyes open in an "idle mode", without performing a cognitive task nor any voluntary physical movements. During the course of the experiment a pulsed electromagnetic field of 20 Hz was applied (similar to the frequency applied in cognitive training programs in said method) over the left and right frontal hemisphere of the brain. Measurement conditions and used instrumentation as described in FIG. 9. The duration of the experiment carried out was 12 minutes. The strength of the electromagnetic field was increased at t=1.5 min from 0% to 100% in 5 increments (20%, 40%, 60%, 80%, 100%) in 1 min steps, whereas 100% in the performed experiment is circa 20 micro Tesla. At t=7.5 min the magnetic field strength was continuously decreased to 0% until t=8.5 min and remained "off" until the end of the experiment. Result: The HEG ratio value started to rise when the electromagnetic field strength was increased and reached a maximum value range between 4% and 5% gain over baseline at pEMF strength of 100% and then slightly dropped to a value of 2% gain over baseline at the end of the experiment.

LIST OF REFERENCES 200 first embodiment of the system (configuration 1)
201 human brain interface device
202 functional control and processing unit
203 database
204 output device
205 VR/AR device
300 second embodiment of the system (configuration 2)
301 Human Brain Interface (HBI) device
302 functional control and processing unit
303 database
304 output device
305 VR/AR device
400 third embodiment of the system (configuration 3)
401 Human Brain Interface (HBI) device
402 functional control and processing unit
403 database
404 output device
500 first embodiment of 501
501 functional components of the Human Brain Interface (HBI) device
502 array-matrix
503 19 multiple compound units
504 22 LED assemblies
505 inside cavity
506 detector optode based on fiber optics
507 spring-loaded mechanism
508 electronic module
600 second embodiment of 601
601 functional components of the Human Brain Interface (HBI) device
602 array-matrix
603 7 multiple compound units 604 7 LED assemblies
605 EMF solenoids
700 process used by the system according to the invention
701 Cognitive Enhancement and Stress Resilience (CESAR)
702 Neuroadaptive Skill Training & Prevention of Cognitive Decline (NADPO)
703 calibration/Baseline setting
704 bio cybernetically controlled process
705 by downloaded user specific data
706 downloaded default set of parameters
707 result evaluation
800 central neuroadaptive process used by the system according to the invention
801 calibration by baseline measurement of multichannel hemoencephalographic brain patterns
802 set of entrainment and feedback output conditions
803 start of the entrainment and feedback program
804 measurement of the hemoencephalographic brain pattern
805 comparison of actual measurement with values from the data base and/or dynamic changes of values
806 adjusting entrainment parameters as a result of the comparison (Loop 1)
807 feedback output presented to the human subject based on the dynamic changes (Loop 2)
808 storing of session log and results in the database

The invention claimed is:

1. A human brain interface device comprising a plurality of compound units, wherein each compound unit comprises:
a housing;
a first measurement unit, for the detection of real time optical signals, wherein the measurement unit is adapted to use near-infrared spectroscopy; and
a entrainment unit for the generation of weak pulsed electromagnetic fields.

2. The device according to claim 1, wherein the plurality of compound units comprise a measurement unit, which is a detector optode and the entrainment unit is a solenoid integrated in a housing with a defined number of small light emitting diodes (LEDs) arranged in a specific geometry.

3. The device according to claim 1, wherein the compound units are arranged in a matrix according to a 10/20 system.

4. The device according to claim 1, wherein the plurality of compound units comprise further:
second measurement units comprising ring electrodes for the detection of real time electrical signals.

5. The device according to claim 1, wherein the housing of the device comprises an inner layer and an outer layer, wherein the outer layer is made of a magnetic shielding material.

6. A brain entrainment system comprising:
the device according to claim 1;
a control and/or processing unit comprising means for:
controlling devices;
acquiring real time signals by measuring of hemoencephalographic brain pattern;
processing, transferring and/or receiving data to and from devices and databases;
and an output device, wherein the output device comprises means for altering the feedback provided to the user according to received output parameters.

7. The system according to claim 6, wherein measurement signals and output parameters are cybernetically controlled in real-time.

8. The system according to claim 6, wherein the output device comprises a machine for physical fitness training.

9. A method of using the system according to claim 6 in a method for training and optimization of brain functions comprising the following steps:
a) calibrating the device by baseline measurements of multichannel hemoencephalographic brain patterns;
b) setting start entrainment and feedback output conditions by loading the brain stimulation data matrix corresponding to a hemoencephalographic brain activation map from a database;
c) starting the entrainment and feedback program;
d) measuring the hemoencephalographic brain pattern;
e) comparing the actual measurement of step d) with values from the database and/or dynamic changes of values within the continuous measurement;
f) adjusting entrainment parameters according to the result of the comparison in step e) (Loop 1);
g) modifying feedback output to the user based on the comparison in step e) (Loop 2) in a continuous dual closed loop until program end;
h) storing session log and results in the database.

10. The method according to claim 9, wherein the start entrainment and feedback output conditions of step b) contains at least one of:
user specific data comprising personalized output parameters, brain activation maps and/or corresponding entrainment parameters.

11. The method according to claim 9, wherein the method further comprises the following steps of:
i) applying interhemispheric-offset stimulation, wherein the oscillation profile applied to the multiple compound units arranged in the matrix at positions 1, 3, 5, 7, 9 are out of phase with those arranged in the matrix at positions 2, 4, 6, 8, 10; and/or random noise stimulation;
j) applying a defined frequency, wherein the oscillation profile applied to the multiple compound units arranged in the matrix at positions 1, 3, 5, 7, 9 are in phase with those arranged in the matrix at positions 2, 4, 6, 8, 10;
k) applying a specific oscillation frequency for a selected position of a compound unit arranged in the matrix.

12. The method according to claim 9, wherein the feedback output in step g) is a VR/AR simulation comprising one or more of the following training scenarios: team sports, individual competitive sports, business and professional activities, interactions between two or more human subjects.

13. The method according to claim 12, wherein the feedback output conditions of step b) comprises a recorded movie or scene consisting of a 360° 3D or Virtual Reality format, wherein the recorded movie or scene is modified in step g).

14. The method according to claim 8, wherein a program extension recalls step b) and stores personalized datasets in step h) including task-optimized brain stimulation parameters remotely from a real or cloud-based database to a computing device, wherein the computing device is a personal computer or a mobile device.

15. The method according to claim 9, wherein the feedback output in step g) is directed to and executed by a training machine for physical fitness.

* * * * *